United States Patent [19]

Hikichi et al.

[11] Patent Number: 5,518,906
[45] Date of Patent: May 21, 1996

[54] PRODUCTION OF D-PANTOIC ACID AND D-PANTOTHENIC ACID

[75] Inventors: Yuichi Hikichi; Takeo Moriya, both of Suita; Hiroshi Miki; Takamasa Yamaguchi, both of Kobe; Ikuo Nogami, Nagaokakyo, all of Japan

[73] Assignee: Takeda Chemical Industries, Ltd., Osaka, Japan

[21] Appl. No.: 480,325

[22] Filed: Jun. 7, 1995

Related U.S. Application Data

[63] Continuation of Ser. No. 121,923, Sep. 16, 1993, abandoned.

[30] Foreign Application Priority Data

Sep. 25, 1992 [JP] Japan .................................... 4-256524

[51] Int. Cl.$^6$ ........................... C12P 13/06; C12N 15/01; C12N 15/70; C12N 9/00
[52] U.S. Cl. ...................... 435/116; 435/69.1; 435/320.1; 435/71.1; 435/71.2; 435/183
[58] Field of Search ...................... 435/116, 69.1, 435/320.1, 71.1, 71.2, 18.3

[56] References Cited

FOREIGN PATENT DOCUMENTS

| | | |
|---|---|---|
| 0493060 | 7/1992 | European Pat. Off. . |
| 4719745 | 5/1972 | Japan . |

OTHER PUBLICATIONS

Maas, "Pantothenate Studies II. Evidence from Mutants for Interferance by Salicylate with Pantoate Synthesis", *J. Bacter.* 63: 227–232 (1952).
Vallari et al "Preparation of High–Specific–Activity D–[3–$^3$H] Pantothenic Acid" *Analyt. Biochem.* 154:671–675 (1986).
Maas et al, "Pantothenate Studies I. Interference by D–Serine and L–Asparte Acid with Pantothenate Synthesis in *E. coli*", *J. Bacter.* 60:733–745 (1950).
Foulds et al "Decreased Permeation of Cephalosporins Through The Outer Membrane of *E. coli* Grown in Salicylates", *Antimicrob. Agnts. Chemo.* 33(4):412–417 (Apr. 1981).
Adelberg et al, "Optimal Conditions for Mutagenesis by N–methyl–N'–nitroso–guanidine in *E. coli* K12", *Biochem.Biophs.Res.Comm* 18:788–795 (1965).
Kawabata et al, "Enzymatic Synthesis of Pantothenic Acid by *Escherichia coli* Cells", *ACS Symp. Ser.* 106 (Immobilized Microb. Cells):133–137 (1979).
Kawabata et al "Enzymatic Synthesis of Pantothenic Acid by *Escherichia coli* cells", *Enzyme Engin.* 5:389–391 (1980).
Teller, *Biosynthesis of Pantoate,* as abstracted in *Diss. Abstr. Int. B* 31(10): 5804, (1971).
Cronan et al "Genetic and Biochemical Analyses of Pantothenate Biosynthesis in *Escherichia coli* in", *J. Bacter.* 149(3):916–922 (Mar. 1982).
Pantothenate Studies—Description Of The Extracted Pantothenate–Synthesizing Enzyme Of *Escherichia Coli* By Werner K. Maas, J. Biol. Chem. 198, 23 (1952) pp. 23–32.
Extracellular Production Of Pantothenic Acid By *Escherichia Coli* Cells—Abstract Papers, Am. Chem. Sec. 176 Meet. Micr. 48/1978, Kawabata et al., abstract #48.

*Primary Examiner*—Robert A. Wax
*Assistant Examiner*—K. Cochrane Carlson
*Attorney, Agent, or Firm*—Foley & Lardner

[57] ABSTRACT

A method of producing D-pantothenic acid or a salt thereof characterized by bring a microbe belonging to the family Enterobacteriaceae having resistance to salicylic acid and capable of producing D-pantothenic acid in the presence of β-alanine in contact with β-alanine, preferably wherein a microbe resistant to α-ketoisovaleric acid and/or α-ketobutyric acid, and/or α-aminobutyric acid and/or β-hydroxyaspartic acid and/or O-methyl-threonine or a microbe transformed with a plasmid DNA carrying the region of a gene involved in biosynthesis of pantothenic acid or a salt thereof or a part thereof, is used, and a method of producing D-pantoic acid or a salt thereof characterized by culturing a microbe resistant to salicylic acid, α-ketoisovaleric acid and/or α-ketobutyric acid and/or α-aminobutyric acid and/or β-hydroxy-aspartic acid and/or O-methyl-threonine and capable of producing D-pantoic acid to accumulate D-pantoic acid or a salt thereof, which is then harvested, and in accordance with these methods, D-pantothenic acid, D-pantoic acid or salts thereof can be efficiently directly obtained microbiologically without using DL-pantoic acid, DL-pantolactone etc. as starting materials.

6 Claims, 1 Drawing Sheet

PRODUCTION OF D-PANTOIC ACID AND D-PANTOTHENIC ACID

This is a continuation of application Ser. No. 08/121,923, filed Sep. 16, 1993, now abandoned.

This invention relates to a new production method and purification method for D-pantoic acid and/or D-pantothenic acid (or a salt thereof), a microbe capable of producing it, and a plasmid DNA having the region of a gene involved in biosynthesis of pantothenic acid or a salt thereof or a part of the region. Pantothenic acid is a useful vitamin substance. D-pantoic acid is a substance useful as an important intermediate for synthesis of pantothenic acid and CoA.

Conventional production methods for D-pantothenic acid (or a salt thereof), an important vitamin substance, include (1) a method wherein D-pantolactone, obtained by optical resolution of DL-pantolactone, and β-alanine (or a salt thereof) are chemically condensed in methanol, (2) a method wherein D-pantothenic acid ester is hydrolyzed to D-pantothenic acid, or a method wherein the D-configuration of DL-pantothenic acid ester is selectively hydrolyzed to D-pantothenic acid, both methods using a microbe or an enzyme (Japanese Patent Unexamined Publication Nos. 228487/1989 and 228488/1989), (3) a method wherein potassium pantoate, β-alanine and ATP are brought into contact with resting cells or a microbial enzyme in Tris buffer to yield pantothenic acid [described in the Journal of Biological Chemistry, Vol. 198, page 23 (1952), the Abstracts of Papers presented at the 176th American Chemical Society National Meeting, Division of Microbial and Biochemical Technology, No. 48 (1.978) and other publications].

Conventional production methods for D-pantoic acid and/or D-pantolactone include (4) a method wherein a resolving agent such as quinine or brucine is used for optical resolution, (5) a method wherein L-pantolactone in DL-pantolactone is decomposed, using a particular microbe, to obtain D-pantolactone alone (Japanese Patent Examined Publication No. 19745/1972), (6) a method wherein L-pantolactone alone in DL-pantolactone is oxidized, using a particular microbe, to ketopantolactone, which is then asymmetrically reduced to D-pantolactone (Japanese Patent Examined Publication No. 293386/1986), (7) a method wherein chemically synthesized ketopantolactone is asymmetrically reduced to D-pantolactone using a particular microbe (Japanese Patent Examined Publication No. 14797/1986), (8) a method wherein the L-configuration in DL-pantolactone is selectively asymmetrically hydrolyzed to L-pantoic acid using a particular microbe (Japanese Patent Unexamined Publication Nos. 152895/1982 and 294092/1987) and (9) a method wherein the D-configuration in DL-pantolactone is selectively asymmetrically hydrolyzed to D-pantoic acid using a particular microbe (Japanese Patent Examined Publication No. 65198/1991).

Concerning how to collect a salt of pantothenic acid, there is a known method wherein calcium chloride is added before crystallization to crystallize a complex salt of calcium pantothenate and calcium chloride at high yield and high purity U.S. Pat. No. 2,957,025, filed by Jonathan O. Brooks on Oct. 18, 1960, Japanese Patent Examined Publication No. 49571/1972 etc.). However, there is no method of removing the calcium chloride from the thus-obtained complex salt to obtain calcium pantothenate at high yield, which complex salt is currently dealt with as the final product.

In industrially producing D-pantothenic acid (including salts thereof; the same applies below), the method (1) requires not only a complex process for synthesizing the starting material DL-pantolactone, but also a troublesome and difficult process for optical resolution thereof. The method (2) has the drawback of requiring of a process for producing D-pantothenic acid ester or DL-pantothenic acid ester from DL-pantolactone. The method (3) is disadvantageous in that expensive ATP and Tris buffer should be used; it yields only a trace amount of pantothenic acid, and is unpractical when using expensive D-pantoic acid (or a salt thereof) as a starting material.

Also, most production methods for D-pantoic acid and/or D-pantolactone are faulty in that they use DL-pantolactone as a starting material, which requires a troublesome synthesizing process. Moreover, the method (4) has drawbacks such as the use of an expensive resolving agent and difficult recovery of D-pantolactone, and the method (5) has a drawback of loss of half the DL-pantolactone produced. In the methods (6), (7), (8) and (9), because of the nature of the microbe used or because of the nature of pantolactone (or pantoic acid), it is very difficult to produce the D-configuration alone at 100% optical purity in the culture broth. Also, the methods (4), (8) and (9) involve an additional troublesome process because the residual L-configuration is recovered, racemized and reused.

Through intensive investigation of industrially advantageous and more efficient production methods for D-pantothenic acid, the present inventors found that culturing a microbe in a medium supplemented with β-alanine results in the formation of D-pantothenic acid. The inventors also found that D-pantoic acid can be accumulated by culturing a strain resistant to salicylic acid, that D-pantothenic acid can be produced at higher concentrations by culturing the strain resistant to salicylic acid in a medium supplemented with β-alanine, and that use of the strain imparted with resistance to α-ketoisovaleric acid, α-ketobutyric acid, α-aminobutyric acid, β-hydroxyaspartic acid and/or O-methylthreonine results in an increased amount of D-pantoic acid and/or D-pantothenic acid produced. Meantime, the inventors investigated application of gene recombination technology to strain breeding, finding that a strain transformed with a plasmid carrying genes involved in biosynthesis of pantothenic acid or a salt thereof accumulates D-pantothenic acid or D-pantoic acid (and/or D-pantolactone) at even higher concentrations in the medium. The inventors made further investigations based on these findings, and developed the present invention.

Accordingly, the present invention relates to

[I] a method for production of D-pantoic acid or a salt thereof which comprises culturing a microbe belonging to the family Enterobacteriaceae having resistance to salicylic acid and capable of producing D-pantoic acid, accumulating D-pantoic acid or a salt thereof, and then harvesting it;

[II] the method for production of [I] using a microbe having at least one species of resistance selected from among resistance to α-ketoisovaleric acid, resistance to α-ketobutyric acid, resistance to α-aminobutyric acid, resistance to β-hydroxyaspartic acid and resistance to O-methylthreonine;

[III] a method for production of D-pantothenic acid or a salt thereof characterized by bringing a microbe belonging to the family Enterobacteriaceae having resistance to salicylic acid and capable of producing D-pantothenic acid into contact with β-alanine;

[IV] the method for production of [III] wherein used is a microbe having at least one species of resistance selected from among resistance to α-ketoisovaleric acid, resistance to α-ketobutyric acid, resistance to αaminobutyric - acid, resistance to β-hydroxyaspartic acid and resistance to O-methylthreonine and

[V] the method for production of [I]–[IV] wherein said microbe is a microbe transformed with a plasmid DNA carrying the region of a gene involved in biosynthesis of pantothenic acid or a salt thereof or a part of the region.

The present invention also provides a transformed microbe and a plasmid for obtaining such a microbe used in these production methods, and a method for purifying and isolating the desired compound.

The present invention has many advantages that it is unnecessary to use DL-pantoic acid, pantolactone etc. as starting materials that the compounds of D-configuration at 100% optical purity can be obtained and that the process for recovering the compounds of L-configuration and that for racemization of it for reuse of the obtained racemic compound are unnecessary.

BRIEF DESCRIPTION OF THE DRAWING

In FIG. 1, E represents EcoRI; EV represents EcoRV; P represents PvuII; B represents BglII.

Figure 1:
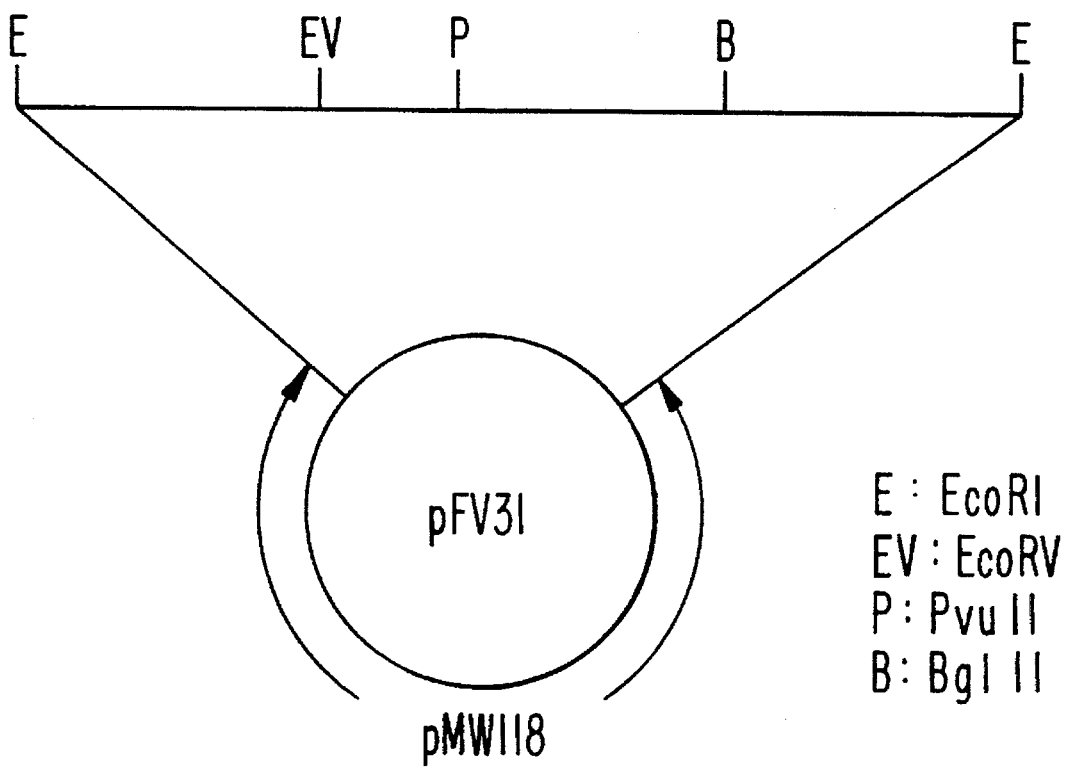
FIG. 1 shows the restriction map of the plasmid pFV31 obtained in Example 3.

The present invention is hereinafter described in detail.

The D-pantoic acid, D-pantothenic acid and β-alanine in the present invention may be salts thereof. When D-pantoic acid, D-pantothenic acid and β-alanine are mentioned in the present specification, not only free forms but also salts thereof are included. Salts of D-pantoic acid, D-pantothenic acid and β-alanine include salts with alkali metals and alkaline earth metals. In any case, the calcium salt, sodium salt and potassium salt are preferred.

The present method of synthesizing D-pantothenic acid and D-pantoic acid is characterized in that a microbe capable of producing pantothenic acid and D-pantoic acid is cultured to microbially produce D-pantoic acid from various carbon sources such as glucose. D-Pantoic acid is accumulated in the medium or is condensed with β-alanine by contacting the microbe with β-alanine by, for example, adding β-alanine to the medium, to produce D-pantothenic acid. Microbes capable of producing D-pantothenic acid or D-pantoic acid in the presence of β-alanine can be used for the present invention. In particular, preferred are microbes belonging to the family Enterobacteriaceae such as microbes belonging to the genera Citrobacter, Shigella, Klebsiella, Enterobacter, Salmonella and Escherichia. More preferably, microbes belonging to the genus Escherichia and those derived therefrom are used for the present invention, including known strains of *Escherichia coli* listed in the List of Cultures, 8th edition, 1988, published by the Institute for Fermentation, Osaka, such as *Escherichia coli* K-12 (IFO 3301) and *Escherichia coli* IFO 3547.

In an attempt to develop a more efficient, more economical production method for D-pantoic acid by de novo synthesis from carbon sources such as sugars using microbes of the genus Escherichia and other genera, the present inventors made investigations and discovered strains capable of producing large amounts of D-pantoic acid when artificially made resistant to salicylic acid. The inventors also found it possible to accumulate large amounts of D-pantothenic acid by keeping such a microbe in contact with β-alanine in a medium containing carbon sources.

In addition, the inventors found that D-pantothenic acid can be produced at higher concentrations by imparting these strains resistant to salicylic acid with resistance to a-ketoisovaleric acid, resistance to α-ketobutyric acid, resistance to α-aminobutyric acid, resistance to β-hydroxyaspartic acid and/or resistance to O-methylthreonine.

Mutants used for the method of the present invention include microbes belonging to the family Enterobacteriaceae, among others, microbes belonging to the genus Escherichia, which are capable of producing D-pantoic acid or D-pantothenic acid. Specifically, such mutants are exemplified by *Escherichia coli* FV5714 (IFO 15368), which is resistant to salicylic acid, *Escherichia coli* FV525 (IFO 15369), which is resistant to both salicylic acid and α-ketoisovaleric acid, *Escherichia coli* FV814 (IFO 15370), which is resistant to salicylic acid, α-ketoisovaleric acid and α-ketobutyric acid, *Escherichia coli* FV 521, which is resistant to salicylic acid, α-ketoisovaleric acid, α-ketobutyric acid and α-aminobutyric acid, *Escherichia coli* FV 221 which is resistant to salicylic acid, α-ketoisovaleric acid, α-ketobutyric acid, and β-hydroxyaspartic acid, *Escherichia coli* FV 6051 and *Escherichia coli* FV 5069 which are resistant to salicylic acid, α-ketoisovaleric acid, α-ketobutyric acid, β-hydroxyaspartic acid and O-methylthreonine.

The mutant FV5714 for the present invention is obtained by subjecting *Escherichia coli* IFO 3547, as a parent strain, to an ordinary mutagenic treatment such as ultraviolet irradiation or treatment with a chemical agent such as N-methyl-N'-nitro-N-nitrosoguanidine, then culturing it on an agar plate medium containing salicylic acid at a concentration such that the parent strain cannot grow, and then separating the colony growing on the plate medium. Similarly, FV525 is obtained by culturing FV5714, as a parent strain, on an agar plate medium containing α-ketoisovaleric acid at a concentration such that the parent strain cannot grow, and then separating the colony growing on the plate medium. FV814 is obtained by culturing FV525, as a parent strain, on an agar plate medium containing α-ketobutyric acid at a concentration such that the parent strain cannot grow, and then separating the colony growing on the plate medium. FV521 is obtained by culturing FV814, as a parent strain, on an agar plate medium containing α-aminobutyric acid at a concentration such that the parent strain cannot grow, and then separating the colony growing on the plate medium. FV 221 is obtained by culturing FV814, as a parent strain, on an agar plate medium containing β-hydroxyaspartic acid at a concentration such that the parent strain cannot grow, and then separating the colony growing on the plate medium. FV 6051 is obtained by culturing FV221, as a parent strain, on an agar plate medium containing O-methylthreonine at a concentration such that the parent strain cannot grow, and then separating the colony growing on the plate medium. FV 5069 is obtained by culturing FV6051, as a parent strain, on an agar plate medium containing α-ketobutyric acid at a concentration such that the parent strain cannot grow, and then separating the colony growing on the plate medium In finally obtaining a strain serving for the object of the present invention, resistances to drugs such as salicylic acid, α-ketoisovaleric acid, α-ketobutyric acid, α-aminobutyric acid, β-hydroxyaspartic acid and O-methylthreonine may be imparted to strains in any order. Also, α-ketoisovaleric acid, α-aminobutyric acid and O-methylthreonine may be replaced with known branched amino acid analogues such as 4-azaleucine, 4-thiaisoleucine and norvaline.

The degrees of resistance of the above-mentioned strains to salicylic acid, α-ketoisovaleric acid, α-ketobutyric acid, α-aminobutyric acid, β-hydroxyasparatic acid or O-methylthreonine are shown in the Experimental Examples below.

Experimental examples

After a medium of the composition shown in Table 1 (hereinafter "%" means "w/v %" unless otherwise stated)

was thermally sterilized at 121° C. for 10 minutes, salicylic acid or α-ketoisovaleric acid, α-ketobutyric acid, α-aminobutyric acid, β-hydroxyaspartic acid or O-methylthreonine previously filtered for sterilization, was added in the concentrations shown in Table 2. The medium was then dispensed to sterile petri dishes of 9 cm diameter. To each of these agar media was added 0.1 ml of a culture broth of the strains selected from *Escherichia coli* IFO 3547, FV5714, FV525, FV814, FV521, FV221, FV6051 and FV5069 as specified in Table 2, cultured in minimal medium for 24 hours, followed by cultivation for 30 hours. Degrees of growth are shown in Table 2.

TABLE 1

| Agar Medium Composition (pH 7.0) | |
|---|---|
| Component | Concentration |
| $Na_2HPO_4$ | 0.6% |
| $KH_2PO_4$ | 0.3% |
| NaCl | 0.05% |
| $NH_4Cl$ | 0.1% |
| Glucose | 0.5% |
| $MgSO_4$ | 1 mM |
| $CaCl_2$ | 0.1 mM |
| Vitamin $B_1$ | 5 μg/ml |
| Agar | 1.5% |

TABLE 2

| Analog Concentration (mg/ml) | Strain Name | | | | | | |
|---|---|---|---|---|---|---|---|
| ① Degree of growth on salicylic acid plate | | | | | | | |
| | IFO 3547 | FV5714 | FV525 | FV814 | | | |
| 0.125 | − | ++ | ++ | ++ | | | |
| 0.25 | − | ± | + | + | | | |
| 0.5 | − | − | ± | ± | | | |
| 1 | − | − | − | − | | | |
| 2 | − | − | − | − | | | |
| ② Degree of growth on α-ketoisovaleric acid plate | | | | | | | |
| | IFO 3547 | FV5714 | FV525 | FV814 | | | |
| 0.625 | ++ | ++ | ++ | ++ | | | |
| 1.25 | + | ++ | ++ | ++ | | | |
| 2.5 | ± | + | + | + | | | |
| 5 | − | ± | + | + | | | |
| 10 | − | − | − | − | | | |
| ③ Degree of growth on α-ketobutyric acid plate | | | | | | | |
| | IFO 3547 | FV5714 | FV525 | FV814 | FV221 | FV6051 | FV5069 |
| 0.125 | ++ | ++ | ++ | ++ | + | + | ++ |
| 0.25 | ++ | ++ | ++ | ++ | + | + | + |
| 0.5 | ± | + | + | ++ | ± | ± | + |
| 1 | − | ± | ± | + | ± | ± | ± |
| 2 | − | − | − | ± | − | − | ± |
| ④ Degree of growth on α-aminobutyric acid plate | | | | | | | |
| | IFO 3547 | FV571 | FV525 | FV814 | FV521 | | |
| 0.125 | ++ | ++ | ++ | ++ | ++ | | |
| 0.25 | + | + | ++ | ++ | ++ | | |
| 0.5 | − | + | + | + | + | | |
| 1 | − | − | ± | + | + | | |
| 2 | − | − | − | − | + | | |
| ⑤ Degree of growth on β-hydroxyaspartic acid plate | | | | | | | |
| | IFO 3547 | FV814 | FV221 | FV6051 | FV5069 | | |
| 0.125 | + | + | ++ | ++ | ++ | | |
| 0.25 | + | + | ++ | ++ | ++ | | |
| 0.5 | − | − | + | ± | + | | |
| 1 | − | − | ± | ± | ± | | |
| 2 | − | − | − | − | − | | |

TABLE 2-continued

| Analog Concentration (mg/ml) | Strain Name | | | | |
|---|---|---|---|---|---|
| | ⑥ Degree of growth on O-methylthreonine plate | | | | |
| | IFO 3547 | FV814 | FV221 | FV6051 | FV5069 |
| 0.0125 | ++ | ++ | ++ | ++ | ++ |
| 0.025 | ++ | ++ | ++ | ++ | ++ |
| 0.05 | + | + | + | ++ | ++ |
| 0.1 | ± | ± | − | ++ | ++ |
| 0.2 | − | − | − | ++ | ++ |

In Table 2, the symbols have the following meanings:

++: Very good growth +: Good growth ±:Poor growth −: No growth

Meantime, on the basis of the production method for D-pantothenic acid described above, the present inventors found that a microbe of the family containing a vector carrying the region of a gene involved in biosynthesis of pantothenic acid or a salt thereof or a part of the region, derived from a chromosome of a microbe of the particular family, accumulates high concentrations of D-pantothenic acid and/or D-pantoic acid.

The gene involved in the pantothenic acid biosynthesis mentioned herein is the panB, panC or panD gene, corresponding to the enzymes ketopantoate hydroxymethyltransferase, pantothenate synthetase and aspartate-α-decarboxylase, respectively.

Donor microbes of such DNA include the above-mentioned microbes, preferably Escherichia microbes capable of producing pantothenic acid. Specifically, they are exemplified by known strains listed in the List of Cultures, 8th edition, 1988, published by the Institute for Fermentation, Osaka, such as *Escherichia coli* K-12 (IFO 3301) and *Escherichia coli* IFO 3547. It is more effective to use the above-mentioned mutants such as *Escherichia coli* FV5714, FV525, FV814, FV521, FV221, FV6051 and FV5069.

Methods of preparing a DNA fragment containing a gene involved in biosynthesis of pantothenic acid or a salt thereof include the method wherein chromosome DNA is first extracted from a donor microbe by a known method such as that described by H. Saito and K. Miura in Biochim. Biophys. Acta, 72, 619 (1963) or a method analogous thereto, after which it is cleaved with restriction enzyme EcoRI. Next, the thus-obtained chromosome DNA fragment containing a gene involved in biosynthesis of pantothenic acid or a salt thereof is inserted into vector DNA.

The vector DNA to be used for the present invention can be selected as appropriate from those which can proliferate in recipient microbes. Plasmids which can proliferate in recipient microbes include, but are not limited to, pSC101 [Proceedings of the National Academy of Sciences of the USA, 70, 3240 (1973)] and pBR322 [Gene, 4, 121 (1978)]; even newly separated or synthesized vector DNAs can be used, as long as the object of the present invention can be accomplished.

Insertion of a DNA fragment containing a gene involved in biosynthesis of pantothenic acid or a salt thereof to these plasmid vectors can be achieved by the known method described by T. Maniatis et al. in Molecular Cloning, A Laboratory Manual, Cold Spring Harbor Laboratory, University of Tokyo Press, 1982, or a method based thereon.

To introduce a plasmid vector carrying a gene involved in biosynthesis of pantothenic acid or a salt thereof to a recipient microbe, a known method of transformation such as that described in the Journal of Molecular Biology, 53, 159 (1979), or a method based thereon, can be used. Examples of the recipient bacterium include known strains such as *Escherichia coli* C600 strain [Bacteriology Review, 36, 525 (1972)].

The transformant containing a plasmid carrying a gene involved in biosynthesis of pantothenic acid or a salt thereof can be selected from among the transformants by transforming a pantothenic acid auxotroph as a DNA recipient and selecting a strain which has become capable of growing in pantothenic acid-free medium as a result of transformation. This selection is facilitated when using a medium allowing selection of strains which serve as plasmid DNA markers. The thus-obtained vector DNA, carrying a gene involved in biosynthesis of pantothenic acid or a salt thereof can be used to extract recombinant DNA from the strain having it and introduce it to another recipient microbe or to prepare a DNA fragment containing a gene involved in biosynthesis of pantothenic acid or a salt thereof from the extracted recombinant DNA and ligate it to another vector plasmid. Example transformants thus obtained include the following:

*Escherichia coli* 3547/pFV31 strain (IFO 15371)

*Escherichia coli* 5714/pFV31 strain (IFO 15372)

*Escherichia coli* 525/pFV31 strain (IFO 15373)

*Escherichia coli* 814/pFV31 strain (IFO 15374) (FERM BP 4401)

*Escherichia coli* 521/pFV31 strain,

*Escherichia coli* 221/pFV31 strain (IFO 15524),

*Escherichia coli* 6051/pFV31 strain (IFO 15525), and

*Escherichia coli* 5069/pFV31 strain (IFO 15526) (FERM BP 4395)

The above *Escherichia coli* 3547/pFV31 strain is obtained by introducing the plasmid pFV31 carrying a gene involved in biosynthesis of pantothenic acid or a salt thereof derived from *Escherichia coli* FV525 into the IFO 3547 strain, the *Escherichia coli* 5714/pFV31 strain results from introduction of pFV31 into the FV5714 strain, the *Escherichia coli* 525/pFV31 strain results from introduction of pFV31 into the FV525 strain, the *Escherichia coli* 814/pFV31 strain results from introduction of pFV31 into the FV814 strain, the *Escherichia coli* 521/pFV31 strain results from introduction of pFV31 into the FV521 strain, the *Escherichia coli* 221/pFV31 strain results from introduction of pFV31 into the FV221 strain, the *Escherichia coli* 6051/pFV31 strain results from introduction of pFV31 into the FV6051 strain and the *Escherichia coli* 5069/pFV31 strain results from introduction of pFV31 into the FV5069 strain.

In the present specification, IFO numbers represent accession numbers at the Institute for Fermentation, Osaka (2-17-85, Jyuso Honmachi, Yodogawa-ku, Osaka-shi), FERM BP numbers representing accession numbers, under the Budapest Treaty, at the Fermentation Research Institute, Agency of Industrial Science and Technology (1-1-3, Higashi, Tsukuba-shi, Ibaraki).

The strain thus obtained can be cultured, continuously or intermittently, by ordinary culturing methods such as standing culture, shaking culture (rotary shaking culture etc.) and aeration spinner culture. The medium used may be of an ordinary composition allowing growth of the microbe used. Carbon sources the microbe can assimilate are appropriately selected from hydrocarbons, oils and fats, fatty acids, organic acids and alcohols, used singly or in combination. For example nitrogen sources include organic nitrogen sources such as peptone, soybean flour, cotton seed flour, corn steep liquor, yeast extracts, meat extracts, malt extracts and urea, and inorganic nitrogen sources such as ammonium sulfate, ammonium chloride, ammonium nitrate and ammonium phosphate, used singly or in combination as necessary. Also, it is advantageous to use monopotassium phosphate or dipotassium phosphate as a phosphorus source. The medium may be normally supplemented with metal salts necessary for growth (e.g., magnesium sulfate) and essential growth factors such as amino acids and vitamins and growth promoters, as well as carbon sources, nitrogen sources and phosphorus sources. To control culture pH and foaming, basic substances such as sodium hydroxide, potassium hydroxide, ammonia and calcium carbonate may be added as appropriate, addition of defoaming agents being effective. These substances may be added as appropriate during cultivation. Oxygen sparging is also effective in keeping the environment under aerobic conditions. It is advantageous to keep culturing temperature normally within the range from 15° to 45° C., preferably 25° to 40° C. Cultivation is continued until the amount of pantothenic acid and/or pantoic acid accumulated has substantially reached maximum; the object of the present invention can be accomplished normally in 6 to 120 hours.

In producing D-pantothenic acid, the starting material β-alanine can be brought into contact with the cells by adding the starting material at an appropriate time before initiation of, or during, strain cultivation, or by adding the starting material to processed cells at an appropriate time. The processed cells mentioned herein include washed cell cultures, and cells included and fixed in acetone powder, polyacrylamide gel or κ-carrageenan. The starting material, in the form of a solution or suspension in an appropriate solvent such as water or in the form of powder, is added at one time or continuously or intermittently over a given period of time.

The concentration of β-alanine added is preferably in accordance with the productivity of the microbe at addition to the medium; with economy in mind, it is preferable to add β-alanine at concentrations of 0.1 to 5 w/v %, more preferably 0.5 to 3 w/v %.

When isolating D-pantothenic acid or a salt thereof from the abovedescribed culture or reaction product, it can be harvested by a routine method. For example, D-pantothenic acid or a salt thereof can be isolated by removing cells from the culture broth and then conducting one or more known procedures such as ion exchange resin treatment, adsorbent treatment with activated charcoal etc., crystallization, salting-out and electrodialysis.

A free form of D-pantothenic acid obtained by the above reaction can be converted to a salt by a conventional method; a salt of D-pantothenic acid obtained by the reaction can be converted to a free form by a conventional method.

For example, calcium pantothenate can be isolated as follows:

Cells are removed from the culture broth containing pantothenic acid or a salt thereof. This liquid is passed through a column of cation exchange resin (e.g., DIAION PK-216 (H type) or PK-228 (H type), both produced by Mitsubishi Chemical Industries) to remove cations and then through a column of artion exchange resin (e.g., DIAION PA-412 (OH type) or WA-30 (OH type), both produced by Mitsubishi Chemical Industries) to remove organic acids more acidic than inorganic anions and pantothenic acid. The effluent (pH 3±1) is adjusted to nearly neutral pH (pit 7±2) by addition of calcium hydroxide, after which activated charcoal (e.g., Shirasagi A, produced by Takeda Chemical Industries) is added, followed by filtration. The resulting filtrate is concentrated, and an appropriate amount of lower alcohol (e.g., methanol, ethanol, isopropanol) is added, after which a seed crystal is added to cause calcium D-pantothenate crystallization, the resulting calcium D-pantothenate crystal being separated and dried. If the yield of this calcium D-pantothenate crystal is insufficient, a complex salt of calcium D-pantothenate and calcium chloride may be crystallized at high yield and high purity by appropriate addition of calcium chloride before crystallization, in accordance with the methods described in U.S. Pat. No. 2,957,025 (filed by Jonathan O. Brooks, Oct. 18, 1960) and Japanese Patent Examined Publication No. 49571/1972. Although the calcium chloride added for this purpose may be a crystal of anhydrous, dihydrous or hexahydrous salt, preference is given to an anhydrous or dihydrous salt. The mount of calcium chloride added is normally 0.5 to 5 times, preferably 1 to 3 times by molar ratio, that of calcium pantothenate. Concerning this complex salt of calcium pantothenate and calcium chloride, U.S. Pat. No. 2,957,025 (filed by Jonathan O. Brooks, Oct. 18, 1960) states that it is non-hygroscopic and effective as an animal feed additive; British Patent No. 933,669 states that it is more stable in tablets than calcium pantothenate.

There have been no reports of methods of calcium chloride removal from the thus-obtained complex salt of calcium D-pantothenate and calcium chloride to obtain calcium D-pantothenate at high yield. The present inventors, after intensive investigation of various methods leading to accomplishment of this purpose, devised a very efficient method of electrodialysis. Specifically, the inventors found that calcium chloride can be efficiently removed from an aqueous solution of the complex salt of calcium D-pantothenate and calcium chloride by electrodialysis using an anion permeable membrane which allows passage of chlorine ions but not pantothenic acid (e.g., the monovalent ion selective permeable membrane Neocepter ACS, produced by Tokuyama Soda) and an aqueous calcium nitrate solution as an electrode liquid. Although the concentration of this complex salt in the aqueous solution is optional, it is normally dissolved within the concentration range normally from 1 to 60% (w/v), preferably 4 to 40% (w/v). The aqueous solution of calcium D-pantothenate obtained by this electrodialytic treatment may be subjected to a common process such as spray drying to yield a powder of calcium D-pantothenate.

Calcium D-pantothenate can thus be efficiently isolated from the culture broth.

D-pantoic acid can be separated by removing cells from the culture broth, adjusting the liquid to pH 1 to 2 with sulfuric acid or hydrochloric acid, derivatizing to pantolactone, a cyclized derivative of pantoic acid, extracting it with a solvent (e.g., isopropyl acetate, ethyl acetate), and then performing concentration and crystallization to yield a crystal. The thus-obtained pantolactone can easily be returned to pantoic acid by addition of sodium hydroxide etc.

EXAMPLES

The present invention is hereinafter described in more detail by means of the following examples, which are only embodiments of the present invention and which do not limit the scope of the present invention in any way.

D-pantothenic acid was quantified by high performance liquid chromatography [column: Shimadzu SCR101H (7.9 mm dia.×30 cm); mobile phase: 0.008N sulfuric acid; flow rate: 0.8 ml/min; detector: differential refractometer] and/or microbial bioassay [indicator strain: *Lactobacillus plantatum* IFO 3070; medium: commercially available pantothenic acid assay medium (produced by DIFCO)]. Quantitative determination and optical purity determination of pantoic acid were conducted by high performance liquid chromatography [column: SUMICHIRAL OA-1200; mobile phase: n-hexane/1,2-dichloroethane/ethanol= 90/8/2; flow rate: 1.0 ml/min; detector: UV] of the ethyl acetate extract after cell removal from the culture broth by centrifugation, addition of 6N hydrochloric acid to the supernatant and subsequent heating in a water bath at 80° C. for 15 minutes (by this operation, pantoic acid in an equilibrium is converted to pantolactone).

Example 1

To a 200 ml conical flask containing 20 ml of a first sterile seed medium of the composition shown in Table 3 was inoculated one platinum loopful of *Escherichia coli* IFO 3547 strain, FV5714 (IFO 15368) strain, FV525 (IFO 15369) strain, FV814 (IFO 15370) strain or FV521 strain from slant medium, followed by rotary shaking culture at 220 rpm and 30° C. for 20 hours. A 1 ml portion of this first seed culture was transferred to a 200 ml ribbed conical flask containing 20 ml of a sterile medium of the composition shown in Table 4, followed by cultivation at 38° C. for 20 hours, immediately after which 2.5 ml of a 54% aqueous glucose solution was added to each flask, followed by cultivation for 24 more hours. The amount and optical purity of pantoic acid produced and the amount of pantothenic acid accumulated, after completion of the cultivation, are given in Table 5.

TABLE 3

Liquid Medium Composition (pH 7.0)

| Component | Concentration |
|---|---|
| Corn steep liquor | 0.5% |
| $(NH_4)_2SO_4$ | 0.5% |
| $MgSO_4.7H_2O$ | 0.01% |
| $KH_2PO_4$ | 0.01% |
| $K_2HPO_4$ | 0.03% |
| $CaCO_3$ | 1.0% |
| Glucose | 5.0% |

TABLE 4

| Liquid Medium ① (pH 7.0) | | Liquid Medium ② (pH 7.0) | |
|---|---|---|---|
| Composition | Concentration | Composition | Concentration |
| Corn steep liquor | 0.2% | Corn steep liquor | 0.2% |
| $(NH_4)_2SO_4$ | 1.5% | $(NH_4)_2SO_4$ | 1.5% |
| $MgSO_4.7H_2O$ | 0.02% | $MgSO_4.7H_2O$ | 0.02% |
| $KH_2PO_4$ | 0.05% | $KH_2PO_4$ | 0.05% |
| $K_2HPO_4$ | 0.1% | $K_2HPO_4$ | 0.1% |
| $CaCO_3$ | 2.0% | $CaCO_3$ | 2.0% |
| Glucose | 9.0% | Glucose | 9.0% |
| | | β-Alanine | 2.0% |

TABLE 5

| | Liquid Medium ① | | Liquid Medium ② |
|---|---|---|---|
| Strain | Amount of Pantoic Acid Produced (mg/ml) | Optical Purity (% ee) | Amount of Pantothenic Acid Produced (mg/ml) |
| *Escherichia coli* | | | |
| IFO 3547 | Not detected | — | 0.1 |
| FV5714 | 1.5 | 100 | 7.0 |
| FV525 | 2.8 | 100 | 11.0 |
| FV814 | 3.0 | 100 | 13.0 |
| FV521 | 3.5 | 100 | 13.9 |

Example 2

To a 200 ml conical flask containing 20 ml of a first sterile seed medium of the composition shown in Table 3 was inoculated with one platinum loopful of *Escherichia coli* FV221 strain, FV6051 strain or FV5069 strain, respectively from slant medium, followed by rotary shaking culture at 220 rpm and 30° C. for 20 hours. A 1 ml portion of this first seed culture was transferred to a 200 ml ribbed conical flask containing 40 ml of a sterile medium of the composition shown in Table 6, followed by cultivation at 38° C. for 20 hours, immediately after which 5 ml of a 54% aqueous glucose solution was added to each flask, followed by cultivation for 24 more hours. The amount and optical purity of pantoic acid produced and the amount of pantothenic acid accumulated, after completion of the cultivation, are given in Table 7.

TABLE 6

| Liquid Medium ① (pH 7.0) | | Liquid Medium ② (pH 7.0) | |
|---|---|---|---|
| Composition | Concentration | Composition | Concentration |
| Corn steep liquor | 2.0% | Corn steep liquor | 2.0% |
| $(NH_4)_2SO_4$ | 1.5% | $(NH_4)_2SO_4$ | 1.5% |
| $MgSO_4.7H_2O$ | 0.02% | $MgSO_4.7H_2O$ | 0.02% |
| $KH_2PO_4$ | 0.05% | $KH_2PO_4$ | 0.05% |
| $K_2HPO_4$ | 0.1% | $K_2HPO_4$ | 0.1% |
| $CaCO_3$ | 3.0% | $CaCO_3$ | 3.0% |
| Glucose | 9.0% | Glucose | 9.0% |
| | | β-Alanine | 2.0% |

TABLE 7

| | Liquid Medium ① | | Liquid Medium ② |
|---|---|---|---|
| Strain | Amount of Pantoic Acid Produced (mg/ml) | Optical Purity (% ee) | Amount of Pantothenic Acid Produced (mg/ml) |
| *Escherichia coli* | | | |
| FV221 | 3.2 | 100 | 15.8 |

TABLE 7-continued

| | Liquid Medium ① | | Liquid Medium ② |
|---|---|---|---|
| Strain | Amount of Pantoic Acid Produced (mg/ml) | Optical Purity (% ee) | Amount of Pantothenic Acid Produced (mg/ml) |
| FV6051 | 3.9 | 100 | 16.3 |
| FV5069 | 4.5 | 100 | 17.9 |

Example 3 i) Preparation of chromosome DNA

*Escherichia coli* FV525 strain, which is capable of producing D-pantothenic acid, was inoculated to 1 liter of L medium (1.0% Bactotrypton, 0.5% yeast extract, 0.5% sodium chloride), followed by overnight cultivation at 37° C. Finally, 3.3 mg of chromosome DNA was obtained from the cells by the method of Saito et al. [Biochim. Biophys. Acta, 72, 619 (1963)], using phenol.

ii) Insertion of chromosome DNA to vector plasmid pMW118

The operations in the following experimentation were in accordance with the method described by T. Maniatis et al. in Molecular Cloning, published by University of Tokyo Press, 1982, unless otherwise stated.

10 μg of the chromosome DNA obtained in term i) above and pMW118 (produced by Nippon Gene) were each cleaved with restriction enzyme EcoRI (produced by Nippon Gene), followed by mixing and ligation in the presence of T4 phage-derived DNA ligase (produced by Nippon Gene).

iii) Cloning of pantothenic acid biosynthesis system gene

Transformation was conducted by the competent cell method. Specifically, competent cells were prepared, using the D-pantothenic acid auxotroph A4C strain (IFO 15251, FERM BP-3677) as derived by nitrosoguanidine mutagenesis from *Escherichia coli* C600 strain. To this suspension was added the plasmid DNA prepared in term ii) above, to incorporate it for transformation. Next, a suspension containing this transformant was spread over a culture plate of an M-9 agar medium (0.6% disodium hydrogen phosphate, 0.3% potassium dihydrogen phosphate, 0.1% ammonium chloride, 0.05% sodium chloride, 1 mM magnesium sulfate, 0.1 mM calcium chloride, 0.5% glucose, 10 μg/ml vitamin $B_1$, 50 μg/ml threonine, 50 μg/ml leucine, 1.5% agar, pH 7.2) supplemented with 50 μg/ml sodium salt of ampicillin, followed by cultivation at 37° C. for 2 days. From the colonies growing on the plate medium, a transformant resistant to ampicillin and capable of producing D-pantothenic acid was obtained. The A4C strain thus transformed with a plasmid carrying an insert derived from the chromosome DNA of *Escherichia coli* FV525 strain was named A4C/pFV31 strain (IFO 15367).

iv) Extraction of plasmid from transformant

Finally, 600 μg of the plasmid was obtained from 1 liter of the culture broth of the transformant *Escherichia coli* A4C/pFV31 strain and named pFV31.

v) Analysis of plasmid pFV31 pFV31 was cleaved with various restriction enzymes and subjected to agarose gel electrophoresis. From the electrophoretic patterns, the restriction enzyme cleavage map shown in FIG. 1 was prepared on the basis of the molecular weight of the lambda phage DNA (produced by Nippon Gene) Hind III digestion product. pFV31 was found to be a recombinant plasmid carrying an about 2.5 kb DNA fragment at the EcoRI site of pMW118.

vi) Re-transformation

To confirm the presence of a gene involved in biosynthesis of pantothenic acid or a salt thereof on pFV31, the α-ketopantoic acid auxotroph A1B strain, β-alanine auxotroph A17D strain and pantothenic acid auxotroph A4C strain, all derived by nitrosoguanidine mutagenesis from *Escherichia coli* C600 strain, were re-transformed with the above plasmid DNA. All resulting transformants were capable of growing on the above M-9 agar medium, demonstrating the presence of the ketopantoate hydroxymethyltransferase, aspartate-α-decarboxylase and patothenate synthetase genes on pFV31.

Furthermore, to confirm the effect on the transformants' capability of producing pantothenic acid, *Escherichia coli* IFO 3547 strain, FV5714, FV525, FV814, FV521, FV221, FV6051 and FV5069 were transformed with pFV31. The thus-obtained transformants were named *Escherichia coli* 3547/pFV31 strain, 5714/pFV31 strain, 525/pFV31 strain, 814/pFV31 strain, 521/pFV31 strain, 221/pFV31 strain, 6051/pFV31 strain and 5069/pFV31 strain, respectively.

Example 4

A liquid medium of the composition shown in Table 3 was thermally sterilized in an autoclave at 121° C. for 15 minutes and then dispensed to 200 ml conical flasks at 20 ml per flask. To each flask was inoculated one platinum loopful of *Escherichia coli* 3547/pFV31 strain, 5714/pFV31 strain, 525/pFV31 strain, 814/pFV31 strain or 521/pFV31 strain as obtained in term vi) in Example 3 from slant medium, followed by rotary shaking culture at 220 rpm and 30° C. for 20 hours. A 1 ml portion of this seed culture was transferred to 20 ml of a medium of the composition shown in Table 4, followed by cultivation at 38° C. for 20 hours in a 200 ml ribbed conical flask, immediately after which 2.5 ml of a 54% aqueous glucose solution was added to each flask, followed by cultivation for 24 more hours. The amount and optical purity of pantoic acid produced and the amount of pantothenic acid accumulated, after completion of the cultivation, are given in Table 8.

TABLE 8

| | Liquid Medium ① | | Liquid Medium ② |
|---|---|---|---|
| Strain | Amount of Pantoic Acid Produced (mg/ml) | Optical Purity (% ee) | Amount of Pantothenic Acid Produced (mg/ml) |
| *Escherichia coli* | | | |
| 3547/pFV31 | 2.2 | 100 | 13.0 |
| 5714/pFV31 | 3.4 | 100 | 14.4 |
| 525/pFV31 | 7.4 | 100 | 25.0 |
| 814/pFV31 | 8.5 | 100 | 31.5 |
| 521/pFV31 | 9.6 | 100 | 34.9 |

Example 5

A liquid medium of the composition shown in Table 3 was thermally sterilized in an autoclave at 121° C. for 15 minutes and then dispensed to 200 ml conical flasks at 20 ml per flask. To each flask was inoculated one platinum loopful of *Escherichia coli* 221/pFV31 strain, 6051/pFV31 or pFV31 strain as obtained in term vi) of Example 3 from slant medium, followed by rotary shaking culture at 220 rpm and 30° C. for 20 hours. A 2 ml portion of this seed culture was transferred to 40 ml of a medium of the composition shown in Table 6, followed by cultivation at 38° C. in a 200 ml ribbed conical flask for 24 hours, immediately after which 5 ml of a 54% aqueous glucose solution was added to each flask, followed by cultivation for another 24 hours. The mount and optical purity of pantoic acid produced and the amount of pantothenic acid accumulated, after completion of the cultivation, are given in Table 9.

TABLE 9

| Strain | Liquid Medium ① | | Liquid Medium ② |
|---|---|---|---|
| | Amount of Pantoic Acid Produced (mg/ml) | Optical Purity (% ee) | Amount of Pantothenic Acid Produced (mg/ml) |
| *Escherichia coli* | | | |
| FV221/pFV31 | 9.8 | 100 | 32.6 |
| FV6051/pFV31 | 10.5 | 100 | 41.3 |
| FV5069/pFV31 | 11.2 | 100 | 45.4 |

Example 6

To a 200 ml conical flask containing 20 ml of a first sterile seed medium of the composition shown in Table 3 was added one platinum loopful of *Escherichia coli* 814/pFV31 strain from slant medium, followed by rotary shaking culture at 220 rpm and 30° C. for 24 hours. A 20 ml portion of this first seed culture was transferred to a 1,000 ml conical flask containing 200 ml of a second sterile seed medium of the same composition, followed by rotary shaking culture at 220 rpm and 30° C. for 24 hours. A 125 ml portion of this second seed culture was transferred to a 5 l jar fermenter containing 2.3 l of a sterile medium containing 250 g of glucose, 12.5 g of corn steep liquor, 37.5 g of ammonium sulfate, 1.25 g of monopotassium phosphate, 2.5 g of dipotassium phosphate, 0.5 g of magnesium sulfate, 75 g of calcium carbonate and 33 g of β-alanine (pH 7.0), followed by cultivation at 38° C. with aeration (0.8 vol/vol/min) and stirring (800 rpm). Over the period from 16 to 62 hours following initiation of cultivation, glucose was continuously added to keep its concentration between 2% and 3%. After 68 hours of cultivation, the final liquid volume was 2.5 l, the amount of D-pantothenic acid produced being 38.5 g/l.

Example 7

A 2.0 l portion (containing 77.0 g of D-pantothenic acid) of the fermentation broth obtained in Example 6 was heated (80° C., 10 min) and then filtered to remove cells and insoluble substances. The filtrate was combined with the washings to yield 2.4 l of liquid, which was passed through a column packed with 600 ml of DIAION PK-216 (H type) and then through a column packed with 340 ml of DIAION PA-412 (OH type), to yield a total of 4.1 l of processed liquid (pH 3.2) as combined with the water effluent. This processed liquid was adjusted to pH 6.8 by the addition of calcium hydroxide, after which 5 g of activated charcoal (Shirasagi A) was added, followed by filtration. The filtrate and the washings were combined to yield a 4.2 l of liquid containing 75.1 g of D-pantothenic acid, from which figure the calcium D-pantothenate content was calculated as 82.0 g. This liquid was used as the starting liquid for crystallization.

A 2.1 l portion (containing 41.0 g of calcium D-pantothenate) of the thus-obtained 4.2 l starting material crystal liquid was concentrated under reduced pressure to a final calcium D-pantothenate concentration of about 43% (w/w). To this concentrate was added 410 ml of methanol, and a 0.5 g seed crystal was added, followed by gradual stirring at 30° C. for 5 hours. The liquid was then kept standing at 5° C. for 14 hours, after which the crystal was separated by filtration and dried. The obtained crystal was found to weigh 6.3 g and have a purity of 98.5%.

Example 8

A 2.1 l portion (containing 41.0 g of calcium D-pantothenate) of the 4.2 l starting material crystal liquid obtained in Example 7 was concentrated under reduced pressure to a final calcium D-pantothenate concentration of about 43% (w/w). To this concentrate was added 100 ml of methanol. After thorough mixing, 310 ml of a methanol solution of 37.94 g of calcium chloride dihydrate was added, and a 0.5 g seed crystal was added, followed by gradual stirring at 50° C. for 5 hours. The crystal was collected by filtration and dried. The obtained crystal was found to weigh 41.95 g and have a composition of 74.3% (w/w) D-pantothenic acid, 13.6% (w/w) Ca and 12.1% (w/w) Cl. This finding demonstrates that this crystal is a complex salt of D-pantothenic acid and calcium chloride in a 1:1 molar ratio.

40 g of this complex salt was dissolved in about 2 l of water and subjected to electrodialysis using an electrodialyzer [TS-2-10 model (Tokuyama Soda); cation permeable membrane: Neocepter CM-1; anion permeable membrane: Neocepter ACS; electrode liquid: 0.2N aqueous calcium nitrate solution; flow rate: 0.3 l/min; voltage: 10 V]. As a result, the calcium chloride was removed to outside the system, and an aqueous calcium D-pantothenate solution (pH 7.0) containing D-pantothenic acid and calcium in a 2:1 molar ratio was obtained. This aqueous calcium D-pantothenate solution was concentrated under reduced pressure to a concentration of about 50% (w/w) and then spray dried, using a spray drier, to yield 34.0 g of a powder of calcium D-pantothenate. This powder had a calcium D-pantothenate purity of 99.8% (w/w) ($[\alpha]_D$=+28.1 (c=5, $H_2O$)).

Example 9

To a 200 ml conical flask containing 20 ml of a first sterile seed medium of the composition shown in Table 3 was added one platinum loopful of *Escherichia coli* 5069/pFV31 strain from slant medium, followed by rotary shaking culture at 220 rpm and 30° C. for 24 hours. A 20 ml portion of this first seed culture was transferred to a 1,000 ml conical flask containing 200 ml of a sterile second seed medium of the same composition, followed by rotary shaking culture at 30° C. for 24 hours. A 75 ml portion of this second seed culture was transferred to a 3 l jar fermenter containing 1.35 l of a sterile medium containing 75 g of glucose, 30 g of corn steep liquor, 22.5 g of ammonium sulfate, 0.75 g of monopotassium phosphate, 1.5 g of dipotassium phosphate, 0.3 g of magnesium sulfate, 45 g of calcium carbonate, 0.75 mg of vitamin $B_1$ and 15 g of β-alanine (pH 7.0), followed by cultivation at 38° C. with aeration (0.8 vol/vol/min) and stirring (700 rpm). Glucose was intermittently added to keep a 5% concentration 15, 27 and 38.5 hours following initiation of culture. Also added were β-alanine to a 1% concentration 27 and 46.5 hours following initiation of culture and 0.75 mg of vitamin $B_1$ 30 and 50 hours following initiation of culture. After 72 hours of culture, the final liquid volume was 1.581, the amount of D-pantothenic acid being 65.4 g/l.

We claim:

1. A method for producing D-pantoic acid or a salt thereof, comprising the steps of
   (1) culturing a microbe which belongs to the genus Escherichia, wherein said microbe is a salicylic acid-resistant mutant derived from a salicylic acid-sensitive parent strain, wherein said mutant can grow even in a minimal medium containing salicylic acid at a concentration which inhibits the growth of said parent strain, and wherein said mutant produces D-pantoic acid, and
   (2) harvesting the accumulated D-pantoic acid or salt thereof.

2. The method according to claim 1 wherein said microbe possesses at least one additional mutation which confers resistance to at least one compound selected from the group consisting of α-ketoisovaleric acid, α-ketobutyric acid, α-aminobutyric acid, β-hydroxyaspartic acid and O-methylthreonine, wherein said microbe having at least one additional mutation can grow even in a minimal medium containing at least one of said compounds at a concentration which inhibits the growth of said salicylic acid-resistant mutant.

3. A method for producing D-pantothenic acid or a salt thereof, comprising the steps of
   (1) culturing a microbe belonging to the genus Escherichia, wherein said microbe is a salicylic acid-resistant mutant derived from a salicylic acid-sensitive parent strain, wherein said mutant can grow even in a minimal medium containing salicylic acid at a concentration which inhibits the growth of said parent strain, and wherein said mutant produces D-pantothenic acid, or a salt thereof, when cultured in a medium containing β-alanine and lacking D-pantoic acid, and
   (2) harvesting the accumulated D-pantothenic acid or a salt thereof.

4. The method according to claim 3 wherein said microbe possesses at least one additional mutation which confers resistance to at least one compound selected from the group consisting of α-ketoisovaleric acid, α-ketobutyric acid, α-aminobutyric acid, β-hydroxyaspartic acid and O-methylthreonine, wherein said microbe having at least one additional mutation can grow even in a minimal medium containing at least one of said compounds at a concentration which inhibits the growth of said salicylic acid-resistant mutant.

5. The method as claimed in claim 1, 2, 3 or 4 wherein said microbe is a microbe which is transformed with a plasmid DNA comprising the genes pan B, pan C and pan D.

6. A mutant microbe derived from a parent strain, wherein said mutant (i) belongs to the genus Escherichia, (ii) has a resistance to salicylic acid when grown in a minimal medium containing salicylic acid at a concentration which inhibits the growth of said parent strain, (iii) is capable of producing D-pantothenic acid in a culture medium containing β-alanine without the addition of D-pantoic acid and (iv) is transformed with a plasmid DNA comprising the genes pan B, pan C, and pan D.

* * * * *